US010227273B2

(12) United States Patent
Miller et al.

(10) Patent No.: US 10,227,273 B2
(45) Date of Patent: Mar. 12, 2019

(54) HYDROCARBON GAS PROCESSING

(71) Applicants: Ortloff Engineers, Ltd., Midland, TX (US); S.M.E. Products, LP, Houston, TX (US)

(72) Inventors: Scott A. Miller, Midland, TX (US); John D. Wilkinson, Midland, TX (US); Joe T. Lynch, Midland, TX (US); Hank M. Hudson, Midland, TX (US); Kyle T. Cuellar, Katy, TX (US); Andrew F. Johnke, Beresford, SD (US); W. Larry Lewis, Tomball, TX (US)

(73) Assignees: Ortloff Engineers, Ltd., Midland, TX (US); S.M.E. Products, LP, Houston, TX (US)

( * ) Notice: Subject to any disclaimer, the term of this patent is extended or adjusted under 35 U.S.C. 154(b) by 0 days.

(21) Appl. No.: 15/688,139

(22) Filed: Aug. 28, 2017

(65) Prior Publication Data

US 2017/0355654 A1 Dec. 14, 2017

Related U.S. Application Data

(62) Division of application No. 14/462,083, filed on Aug. 18, 2014, now Pat. No. 9,783,470.

(Continued)

(51) Int. Cl.
*C07C 7/09* (2006.01)
*B01D 3/26* (2006.01)

(Continued)

(52) U.S. Cl.
CPC .................. *C07C 7/09* (2013.01); *B01D 3/26* (2013.01); *B01D 3/32* (2013.01); *B01D 3/322* (2013.01);

(Continued)

(58) Field of Classification Search
None
See application file for complete search history.

(56) References Cited

U.S. PATENT DOCUMENTS 33,408 A 10/1861 Turner et al.
311,402 A 1/1885 Withington
(Continued)

OTHER PUBLICATIONS

Supplemental Notice of Allowability issued in U.S. Appl. No. 12/689,616, dated Feb. 10, 2015 (12 pages).

(Continued)

*Primary Examiner* — Tam M Nguyen
(74) *Attorney, Agent, or Firm* — Venable LLP

(57) ABSTRACT

A process and an apparatus are disclosed for a compact processing assembly to remove $C_5$ and heavier hydrocarbon components from a hydrocarbon gas stream. The hydrocarbon gas stream is expanded to lower pressure and supplied to the processing assembly between an absorbing means and a mass transfer means. A distillation vapor stream is collected from the upper region of the absorbing means and cooled in a first heat and mass transfer means inside the processing assembly to partially condense it, forming a residual vapor stream and a condensed stream. The condensed stream is supplied to the absorbing means at its top feed point. A distillation liquid stream is collected from the lower region of the mass transfer means and directed into a second heat and mass transfer means inside the processing assembly to heat it and strip out its volatile components.

9 Claims, 6 Drawing Sheets

Related U.S. Application Data

(60) Provisional application No. 61/879,308, filed on Sep. 18, 2013, provisional application No. 61/876,415, filed on Sep. 11, 2013.

(51) Int. Cl.
| | |
|---|---|
| *F25J 1/00* | (2006.01) |
| *B01D 3/32* | (2006.01) |
| *B01D 5/00* | (2006.01) |
| *C10L 3/06* | (2006.01) |
| *C10G 5/06* | (2006.01) |

(52) U.S. Cl.
CPC ............. *B01D 5/0063* (2013.01); *C10G 5/06* (2013.01); *C10L 3/06* (2013.01); *F25J 1/0022* (2013.01); *C10L 2290/06* (2013.01); *C10L 2290/48* (2013.01); *C10L 2290/541* (2013.01); *C10L 2290/543* (2013.01); *C10L 2290/545* (2013.01)

(56) References Cited

U.S. PATENT DOCUMENTS

| | | | |
|---|---|---|---|
| 3,292,380 A | 12/1966 | Bucklin | |
| 3,292,980 A | 12/1966 | Gustafsson et al. | |
| 3,477,915 A | 11/1969 | Gantt et al. | |
| 3,508,412 A | 4/1970 | Yearout | |
| 3,516,261 A | 6/1970 | Hoffman | |
| 3,625,017 A | 12/1971 | Hoffman | |
| 3,797,261 A | 3/1974 | Juncker et al. | |
| 3,983,711 A | 10/1976 | Solomon | |
| 4,061,481 A | 12/1977 | Campbell et al. | |
| 4,127,009 A | 11/1978 | Phillips | |
| 4,140,504 A | 2/1979 | Campbell et al. | |
| 4,157,904 A | 6/1979 | Campbell et al. | |
| 4,171,964 A | 10/1979 | Campbell et al. | |
| 4,185,978 A | 1/1980 | McGalliard et al. | |
| 4,251,249 A | 2/1981 | Gulsby | |
| 4,278,457 A | 7/1981 | Campbell et al. | |
| 4,519,824 A | 5/1985 | Huebel | |
| 4,617,039 A | 10/1986 | Buck | |
| 4,687,499 A | 8/1987 | Aghili | |
| 4,688,399 A | 8/1987 | Reimann | |
| 4,689,063 A | 8/1987 | Paradowski et al. | |
| 4,690,702 A | 9/1987 | Paradowski et al. | |
| 4,854,955 A | 8/1989 | Campbell et al. | |
| 4,869,740 A | 9/1989 | Campbell et al. | |
| 4,889,545 A | 12/1989 | Campbell et al. | |
| 5,255,528 A | 10/1993 | Dao | |
| 5,275,005 A | 1/1994 | Campbell et al. | |
| 5,282,507 A | 2/1994 | Tongu et al. | |
| 5,316,628 A | 5/1994 | Collin et al. | |
| 5,335,504 A | 8/1994 | Durr et al. | |
| 5,339,654 A | 8/1994 | Cook et al. | |
| 5,367,884 A | 11/1994 | Phillips et al. | |
| 5,410,885 A | 5/1995 | Smolarek et al. | |
| 5,555,748 A | 9/1996 | Campbell et al. | |
| 5,566,554 A | 10/1996 | Vijayaraghavan et al. | |
| 5,568,737 A | 10/1996 | Campbell et al. | |
| 5,675,054 A | 10/1997 | Manley et al. | |
| 5,685,170 A | 11/1997 | Sorensen | |
| 5,713,216 A | 2/1998 | Erickson | |
| 5,771,712 A | 6/1998 | Campbell et al. | |
| 5,799,507 A | 9/1998 | Wilkinson et al. | |
| 5,881,569 A | 3/1999 | Campbell et al. | |
| 5,890,377 A | 4/1999 | Foglietta | |
| 5,890,378 A | 4/1999 | Rambo et al. | |
| 5,942,164 A | 8/1999 | Tran | |
| 5,983,664 A | 11/1999 | Campbell et al. | |
| 6,077,985 A | 6/2000 | Stork | |
| 6,182,469 B1 | 2/2001 | Campbell et al. | |
| 6,361,582 B1 | 3/2002 | Pinnau et al. | |
| 6,516,631 B1 | 2/2003 | Trebble | |
| 6,565,626 B1 | 5/2003 | Baker et al. | |
| 6,578,379 B2 | 6/2003 | Paradowski | |
| 6,694,775 B1 | 2/2004 | Higginbotham et al. | |
| 6,712,880 B2 | 3/2004 | Fogietta et al. | |
| 6,742,358 B2 | 6/2004 | Wilkinson et al. | |
| 6,915,662 B2 | 7/2005 | Wilkinson et al. | |
| 6,945,075 B2 | 9/2005 | Wilkinson et al. | |
| 7,010,937 B2 | 3/2006 | Wilkinson et al. | |
| 7,165,423 B2 | 1/2007 | Winningham | |
| 7,191,617 B2 | 3/2007 | Cuellar et al. | |
| 7,204,100 B2 | 4/2007 | Wilkinson et al. | |
| 7,210,311 B2 | 5/2007 | Wilkinson et al. | |
| 7,219,513 B1 | 5/2007 | Mostafa | |
| 7,565,815 B2 | 7/2009 | Wilkinson et al. | |
| 7,631,516 B2 | 12/2009 | Cuellar et al. | |
| 7,713,497 B2 | 5/2010 | Mak | |
| 8,156,758 B2 | 4/2012 | Denton et al. | |
| 8,434,325 B2 | 5/2013 | Martinez et al. | |
| 8,590,340 B2 | 11/2013 | Pitman et al. | |
| 8,881,549 B2 | 11/2014 | Johnke et al. | |
| 8,919,148 B2 | 12/2014 | Wilkinson et al. | |
| 9,021,831 B2 | 5/2015 | Johnke et al. | |
| 9,021,832 B2 | 5/2015 | Pierce et al. | |
| 9,052,136 B2 | 6/2015 | Johnke et al. | |
| 9,052,137 B2 | 6/2015 | Johnke et al. | |
| 9,057,558 B2 | 6/2015 | Johnke et al. | |
| 9,068,774 B2 | 6/2015 | Johnke et al. | |
| 9,074,814 B2 | 7/2015 | Johnke et al. | |
| 9,080,810 B2 | 7/2015 | Pitman et al. | |
| 9,080,811 B2 | 7/2015 | Johnke et al. | |
| 2001/0008073 A1 | 7/2001 | Finn et al. | |
| 2002/0166336 A1 | 11/2002 | Wilkinson et al. | |
| 2004/0079107 A1 | 4/2004 | Wilkinson et al. | |
| 2004/0172967 A1 | 9/2004 | Patel et al. | |
| 2005/0229634 A1 | 10/2005 | Huebel et al. | |
| 2005/0247078 A1 | 11/2005 | Wilkinson et al. | |
| 2005/0268649 A1 | 12/2005 | Wilkinson et al. | |
| 2006/0004242 A1 | 1/2006 | Verma et al. | |
| 2006/0032269 A1 | 2/2006 | Cuellar et al. | |
| 2006/0086139 A1 | 4/2006 | Eaton et al. | |
| 2006/0283207 A1 | 12/2006 | Pitman et al. | |
| 2008/0000265 A1 | 1/2008 | Cuellar et al. | |
| 2008/0078205 A1 | 4/2008 | Cuellar et al. | |
| 2008/0190136 A1 | 8/2008 | Pitman et al. | |
| 2008/0271480 A1 | 11/2008 | Mak | |
| 2009/0107175 A1 | 4/2009 | Patel et al. | |
| 2009/0293538 A1 | 12/2009 | Wilkinson et al. | |
| 2010/0251764 A1 | 10/2010 | Johnke et al. | |
| 2010/0275647 A1 | 11/2010 | Johnke et al. | |
| 2010/0287983 A1 | 11/2010 | Johnke et al. | |
| 2010/0287984 A1 | 11/2010 | Johnke et al. | |
| 2010/0326134 A1 | 12/2010 | Johnke et al. | |
| 2011/0067441 A1 | 3/2011 | Martinez et al. | |
| 2011/0067442 A1 | 3/2011 | Martinez et al. | |
| 2011/0067443 A1 | 3/2011 | Martinez et al. | |
| 2011/0226011 A1 | 9/2011 | Johnke et al. | |
| 2011/0226013 A1* | 9/2011 | Johnke .................. F25J 3/0209 62/620 |
| 2011/0232328 A1 | 9/2011 | Johnke et al. | |
| 2012/0137726 A1 | 6/2012 | Currence et al. | |
| 2015/0073194 A1 | 3/2015 | Hudson et al. | |
| 2015/0073195 A1 | 3/2015 | Lynch et al. | |
| 2015/0073196 A1 | 3/2015 | Miller et al. | |
| 2015/0315106 A2 | 11/2015 | Miller et al. | |
| 2017/0067684 A1 | 3/2017 | Manning | |

OTHER PUBLICATIONS

Comments on Statement of Reasons for Allowance filed in U.S. Appl. No. 12/689,616, dated Mar. 3, 2015 (7 pages).

Response and Statement of Interview filed in U.S. Appl. No. 13/052,575, dated Mar. 16, 2015 (37 pages).

Response and Statement of Interview filed in U.S. Appl. No. 13/052,348, dated Mar. 17, 2015 (37 pages).

Response and Statement of Interview filed in U.S. Appl. No. 13/053,792, dated Mar. 18, 2015 (37 pages).

Response Statement of Interview and Petition for Extension of Time filed in U.S. Appl. No. 13/051,682, dated Mar. 19, 2015 (37 pages).

(56) References Cited

OTHER PUBLICATIONS

Response, Statement of Interview and Petition for Extension of Time filed in U.S. Appl. No. 13/048,315, dated Mar. 20, 2015 (93 pages).
Amendment and Statement of Interview filed in U.S. Appl. No. 13/052,348, dated Mar. 26, 2015 (23 pages).
Amendment and Statement of Interview filed in U.S. Appl. No. 13/051,682, dated Mar. 26, 2015 (29 pages).
Amendment and Statement of Interview filed in U.S. Appl. No. 13/053,792, dated Mar. 26, 2015 (25 pages).
Amendment and Statement of Interview filed in U.S. Appl. No. 13/052,575, dated Mar. 26, 2015 (20 pages).
Notice of Allowance and Fee(s) Due issued in U.S. Appl. No. 12/689,616, dated Jan. 9, 2015 (15 pages).
Comments on Statement of Reasons for Allowance filed in U.S. Appl. No. 12/689,616, dated Jan. 30, 2015 (8 pages).
Office Action issued in U.S. Appl. No. 13/052,348, dated Dec. 17, 2014 (13 pages).
Office Action issued in U.S. Appl. No. 13/051,682, dated Dec. 18, 2014 (13 pages).
Office Action issued in U.S. Appl. No. 13/053,792, dated Dec. 18, 2014 (20 pages).
Office Action issued in U.S. Appl. No. 13/052,575, dated Dec. 16, 2014 (16 pages).
Advisory Action Before the Filing of an Appeal Brief issued in U.S. Appl. No. 12/689,616, dated Nov. 28, 2014 (3 pages).
Submission Under 37 C.F.R. § 1.114, Statement of Interview, and Petition for Extension of Time filed in U.S. Appl. No. 12/689,616, dated Dec. 8, 2014 (39 pages).
International Search Report and Written Opinion issued in International Application No. PCT/US2011/028872 dated May 18, 2011—7 pages.
International Search Report and Written Opinion issued in International Application No. PCT/US2011/29234 dated May 20, 2011—30 pages.
International Search Report and Written Opinion issued in International Application No. PCT/US2011/029034 dated Jul. 27, 2011—40 pages.
International Search Report and Written Opinion issued in International Application No. PCT/US2011/029409 dated May 17, 2011—15 pages.
International Search Report and Written Opinion issued in International Application No. PCT/US2011/029239 dated May 20, 2011—21 pages.

E. Ross Mowrey, "Efficient, High Recovery of Liquids From Natural Gas Utilizing a High Pressure Absorber," Proceedings of the Eighty-First Annual Convention of the Gas Processors Association, Dallas, Texas, Mar. 11-13, 2002.
"Dew Point Control Gas Conditioning Units," SME Products Brochure, Gas Processors Assoc. Conference (Apr. 5, 2009).
"Fuel Gas Conditioning Units for Compressor Engines," SME Products Brochure, Gas Processors Assoc. Conference (Apr. 5, 2009).
"P&ID Fuel Gas Conditioner," Drawing No. SMEP-901, Date Drawn: Aug. 29, 2007, SME, available at http://www.sme-llc.com/sme.cfm?a=prd&catID=44&prdID=155 (Apr. 24, 2009).
"Fuel Gas Conditioner Preliminary Arrangement," Drawing No. SMP-1007-00, Date Drawn: Nov. 11, 2008, SME, available at http://www.sme-llc.com/sme.cfm?a=prd&catID=44&prdID=155 (Apr. 24, 2009).
"Product: Fuel Gas Conditioning Units," SME Associates,m LLC, available at http://www.sme-llc.com/sme.cfm?a=prd&catID=58&subID=44&prdID=155 (Apr. 24, 2009).
International Search Report and Written Opinion issued in International Application No. PCT/US2010/21364 dated Mar. 29, 2010—20 pages.
International Search Report and Written Opinion issued in International Application No. PCT/US2010/26185 dated Jul. 9, 2010—20 pages.
International Search Report and Written Opinion issued in corresponding International Application No. PCT/US2010/29331 dated Jul. 2, 2010—15 pages.
International Search Report and Written Opinion issued in International Application No. PCT/US2010/33374 dated Jul. 19, 2010—18 pages.
International Search Report and Written Opinion issued in International Application No. PCT/US2010/35121 dated Jul. 19, 2010—18 pages.
International Search Report and Written Opinion issued in International Application No. PCT/US2010/37098 dated Aug. 17, 2010—12 pages.
International Search Report and Written Opinion issued in International Application No. PCT/US14/51544 dated Nov. 24, 2014—16 pages.
Huebel, R., et al., "New NGL-Recovery Process Provides Viable Alternative", Oil & Gas Journal, Jan. 9, 2012 (9 pages).
International Search Report and Written Opinion issued in International Application No. PCT/US14/51547 dated Nov. 24, 2014—21 pages.
International Search Report and Written Opinion issued in International Application No. PCT/US14/51548 dated Nov. 5, 2014—24 pages.

* cited by examiner

HYDROCARBON GAS PROCESSING

The present application is a division of U.S. patent application Ser. No. 14/462,083, filed Aug. 18, 2014 (published as US Patent Application Publication No. 2015-0073196 A1) which claims the benefit of priority under 35 U.S.C. § 119(e) to U.S. Provisional Application No. 61/879,308 filed Sep. 18, 2013, and U.S. Provisional Application No. 61/876,415 filed Sep. 11, 2013, the entire disclosure of each of which is incorporated by reference herein.

BACKGROUND OF THE INVENTION

Natural gas is typically recovered from wells drilled into underground reservoirs. It usually has a major proportion of methane, i.e., methane comprises at least 50 mole percent of the gas. Depending on the particular underground reservoir, the natural gas also contains relatively lesser amounts of heavier hydrocarbons such as ethane, propane, butanes, pentanes and the like, as well as water, hydrogen, nitrogen, carbon dioxide, and other gases. A typical analysis of a natural gas stream to be processed in accordance with this invention would be, in approximate mole percent, 89.2% methane, 4.9% ethane and other $C_2$ components, 2.6% propane and other $C_3$ components, 0.4% iso-butane, 1.3% normal butane, and 0.6% pentanes plus, with the balance made up of nitrogen and carbon dioxide. Sulfur containing gases are also sometimes present.

Most natural gas is handled in gaseous form. The most common means for transporting natural gas from the wellhead to gas processing plants and thence to the natural gas consumers is in high-pressure gas transmission pipelines. In a number of circumstances, however, it has been found necessary and/or desirable to liquefy the natural gas either for transport or for use. In remote locations, for instance, there is often no pipeline infrastructure that would allow for convenient transportation of the natural gas to market. In such cases, the much lower specific volume of liquefied natural gas (LNG) relative to natural gas in the gaseous state can greatly reduce transportation costs by allowing delivery of the LNG using cargo ships and transport trucks.

A relatively recent concept for commercializing natural gas from remote locations is to install a liquefaction plant on an offshore platform or on a ship (commonly referred to as floating LNG or FLNG) to allow moving the facility to another location when the gas reservoir is depleted. Deck space is at a premium for both of these, because each increment of deck space requires a very large quantity of supporting structure (and hull volume in the case of FLNG). As a result, great emphasis is placed on minimizing the "footprint" of each processing step in order to minimize the investment cost and thereby maximize the number of gas reservoirs in remote locations that can be economically produced.

For remote locations such as those contemplated here, recovery of the various hydrocarbons heavier than methane as separate products is generally not economically viable since there is usually no means of transporting and selling the resultant hydrocarbon product streams. Instead, to the largest extent possible, these heavier hydrocarbons are liquefied along with the methane and sold as part of the LNG product. However, some degree of heavier hydrocarbon removal is often required prior to liquefying the natural gas because there are usually limitations on the heating value of the re-vaporized gas when it is subsequently distributed from the LNG receiving terminal. In addition, hydrocarbons heavier than $C_5$ or $C_6$ (particularly aromatic hydrocarbons) generally must be removed upstream of the liquefaction step to avoid plugging inside the liquefaction plant caused by freezing of these heavier hydrocarbons. For these reasons, it is typical to include a processing step to remove these hydrocarbons ("heavy ends removal") before liquefying the natural gas.

Available processes for removing these heavier hydrocarbons include those based upon cooling and refrigeration of gas, oil absorption, and refrigerated oil absorption. Additionally, cryogenic processes have become popular because of the availability of economical equipment that produces power while simultaneously expanding and extracting heat from the gas being processed. Depending upon the pressure of the gas source, the richness (ethane, ethylene, and heavier hydrocarbons content) of the gas, and the desired end products, each of these processes or a combination thereof may be employed.

The cryogenic expansion process is now generally preferred for removing heavy hydrocarbons from natural gas because it provides maximum simplicity with ease of startup, operating flexibility, good efficiency, safety, and good reliability. U.S. Pat. Nos. 3,292,380; 4,061,481; 4,140,504; 4,157,904; 4,171,964; 4,185,978; 4,251,249; 4,278,457; 4,519,824; 4,617,039; 4,687,499; 4,689,063; 4,690,702; 4,854,955; 4,869,740; 4,889,545; 5,275,005; 5,555,748; 5,566,554; 5,568,737; 5,771,712; 5,799,507; 5,881,569; 5,890,378; 5,983,664; 6,182,469; 6,578,379; 6,712,880; 6,742,358; 6,915,662; 6,945,075; 7,010,937; 7,191,617; 7,204,100; 7,210,311; 7,219,513; 7,565,815; 8,590,340; reissue U.S. Pat. No. 33,408; and co-pending application Ser. Nos. 11/430,412; 11/839,693; 12/206,230; 12/487,078; 12/689,616; 12/717,394; 12/750,862; 12/772,472; 12/781,259; 12/868,993; 12/869,007; 12/869,139; 12/979,563; 13/048,315; 13/051,682; 13/052,348; 13/052,575; and 13/053,792 describe relevant processes (although the description of the present invention in some cases is based on different processing conditions than those described in the cited U.S. Patents and co-pending applications).

The present invention is a novel means of removing heavier hydrocarbon components from natural gas that combines what heretofore have been individual equipment items into a common housing, thereby reducing the plot space requirements, the capital cost of the plant, and (more importantly) the capital cost of the associated platform or ship. In addition, the more compact arrangement also eliminates much of the piping used to interconnect the individual equipment items in traditional plant designs, further reducing capital cost and also eliminating the associated flanged piping connections. Since piping flanges are a potential leak source for hydrocarbons (which are volatile organic compounds, VOCs, that contribute to greenhouse gases and may also be precursors to atmospheric ozone formation), eliminating these flanges reduces the potential for atmospheric emissions that may damage the environment.

For a better understanding of the present invention, reference is made to the following examples and drawings. Referring to the drawings.

In the following explanation of the above figures, tables are provided summarizing flow rates calculated for representative process conditions. In the tables appearing herein, the values for flow rates (in moles per hour) have been rounded to the nearest whole number for convenience. The total stream rates shown in the tables include all non-hydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

For convenience, process parameters are reported in both the traditional British units and in the units of the Systeme International d'Unités (SI). The molar flow rates given in the tables may be interpreted as either pound moles per hour or kilogram moles per hour. The energy consumptions reported as horsepower (HP) and/or thousand British Thermal Units per hour (MBTU/Hr) correspond to the stated molar flow rates in pound moles per hour. The energy consumptions reported as kilowatts (kW) correspond to the stated molar flow rates in kilogram moles per hour.

DESCRIPTION OF THE PRIOR ART

Figure 1:
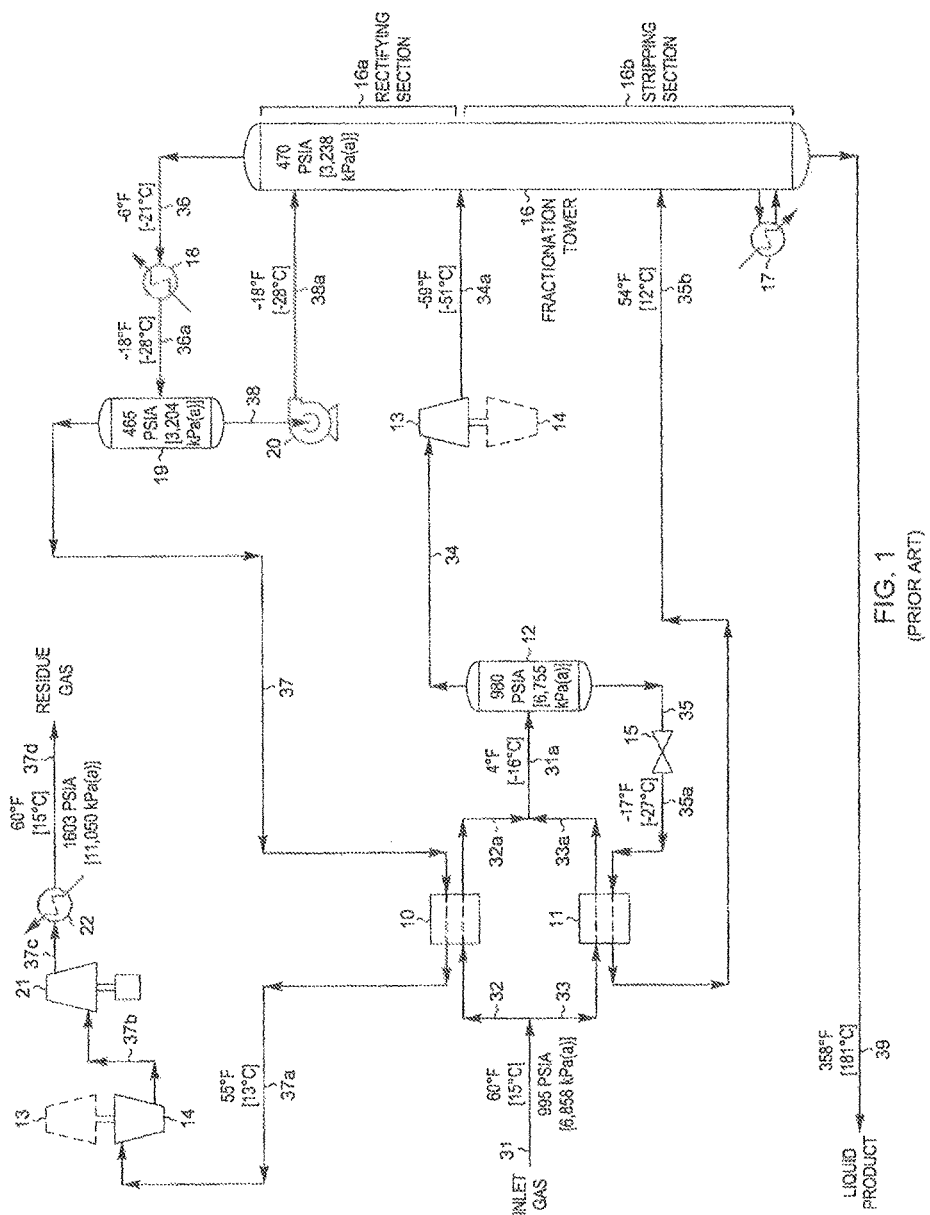
FIGS. 1 and 2 are flow diagrams of prior art heavy ends removal processes for a natural gas liquefaction plant.

FIG. 1 is a process flow diagram showing the design of a processing plant to remove heavier hydrocarbon components from a natural gas stream using a prior art process. In this simulation of the process, inlet gas enters the plant at 60° F. [15° C.] and 995 psia [6,858 kPa(a)] as stream 31. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose.

The feed stream 31 is divided into two portions, streams 32 and 33. Stream 32 is cooled in heat exchanger 10 by heat exchange with cool residue gas stream 37, while stream 33 is cooled in heat exchanger 11 by heat exchange with flash expanded liquids (stream 35a). Streams 32a and 33a recombine to form stream 31a, which enters separator 12 at 4° F. [−16° C.] and 980 psia [6,755 kPa(a)] where the vapor (stream 34) is separated from the condensed liquid (stream 35).

The vapor from separator 12 (stream 34) enters a work expansion machine 13 in which mechanical energy is extracted from this portion of the high pressure feed. The machine 13 expands the vapor substantially isentropically to the operating pressure (approximately 470 psia [3,238 kPa(a)]) of fractionation tower 16, with the work expansion cooling the expanded stream 34a to a temperature of approximately −59° F. [−51° C.]. The typical commercially available expanders are capable of recovering on the order of 80-85% of the work theoretically available in an ideal isentropic expansion. The work recovered is often used to drive a centrifugal compressor (such as item 14) that can be used to re-compress the heated residue gas stream (stream 37a), for example. The partially condensed expanded stream 34a is thereafter supplied as feed to fractionation tower 16 at an upper mid-column feed point. The separator liquid (stream 35) is expanded to slightly above the operating pressure of fractionation tower 16 by expansion valve 15, then heated from −17° F. [−27° C.] to 54° F. [12° C.] in heat exchanger 11 as described earlier before stream 35b is supplied to fractionation tower 16 at a lower mid-column feed point.

Fractionation tower 16 is a conventional distillation column containing a plurality of vertically spaced trays, one or more packed beds, or some combination of trays and packing. As is often the case, the fractionation tower may consist of two sections, an upper rectifying section 16a and a lower stripping section 16b. The upper rectifying section 16a contains trays and/or packing and provides the necessary contact between the vapor rising from the lower distillation or stripping section 16b and a liquid stream (reflux) to remove the heavier hydrocarbon components from the vapor. The lower, stripping section 16b also contains trays and/or packing and provides the necessary contact between the liquids falling downward and the vapors rising upward. The stripping section 16b also includes at least one reboiler (such as the reboiler 17) which heats and vaporizes a portion of the liquids flowing down the column to provide the stripping vapors which flow up the column to strip the liquid product, stream 39, of lighter hydrocarbon components so that it contains only the heavier hydrocarbon components that were in the natural gas feed stream (stream 31), whereupon it exits the bottom of the tower at 358° F. [181° C.].

The column overhead vapor (stream 36) is withdrawn from the top of tower 16 at −6° F. [−21° C.] and is cooled to −18° F. [−28° C.] and partially condensed (stream 36a) in heat exchanger 18 using a refrigerant. The operating pressure in reflux separator 19 is maintained slightly below the operating pressure of tower 16. This provides the driving force which causes overhead vapor stream 36 to flow through reflux condenser 18 and thence into the reflux separator 19 wherein the condensed liquid (stream 38) is separated from the uncondensed vapor (stream 37). The liquid stream 38 from reflux separator 19 is pumped by reflux pump 20 to a pressure slightly above the operating pressure of tower 16, and stream 38a is then supplied as cold top column feed (reflux) to tower 16. This cold liquid reflux absorbs and condenses the heavier hydrocarbon components in the vapors rising up in rectifying section 16a of tower 16. The residue gas (vapor stream 37) passes countercurrently to the incoming feed gas in heat exchanger 10 where it is heated to 55° F. [13° C.] as it provides cooling as previously described. The residue gas is then re-compressed in two stages, compressor 14 driven by expansion machine 13 and compressor 21 driven by a supplemental power source. (In the FIG. 1 process, compressor 21 consists of two compression stages with intercooling between the stages.) After stream 37c is cooled in discharge cooler 22, the residue gas product (stream 37d) flows to the sales gas pipeline or to the liquefaction plant at 1603 psia [11,050 kPa(a)].

A summary of stream flow rates and energy consumption for the process illustrated in FIG. 1 is set forth in the following table:

TABLE I (FIG. 1)
Stream Flow Summary - Lb. Moles/Hr [kg moles/Hr]

| Stream | Methane | Ethane | Propane | Butanes | Pentanes+ | Total |
| --- | --- | --- | --- | --- | --- | --- |
| 31 | 29,885 | 1,626 | 869 | 574 | 189 | 33,501 |
| 34 | 29,570 | 1,555 | 769 | 428 | 77 | 32,756 |

TABLE I-continued (FIG. 1)
Stream Flow Summary - Lb. Moles/Hr [kg moles/Hr]

| | | | | | | |
|---|---|---|---|---|---|---|
| 35 | 315 | 71 | 100 | 146 | 112 | 745 |
| 36 | 29,987 | 1,666 | 959 | 586 | 7 | 33,564 |
| 38 | 102 | 40 | 91 | 164 | 4 | 402 |
| 37 | 29,885 | 1,626 | 868 | 422 | 3 | 33,162 |
| 39 | 0 | 0 | 1 | 152 | 186 | 339 |

Recoveries*

| | |
|---|---|
| Butanes | 26.52% |
| Pentanes+ | 98.42% |

Power

| | | |
|---|---|---|
| Residue Gas Compression | 15,290 HP | [25,137 kW] |
| Refrigerant Compression | 861 HP | [1,415 kW] |
| Total Compression | 16,151 HP | [26,552 kW] |

*(Based on un-rounded flow rates)

Figure 2:
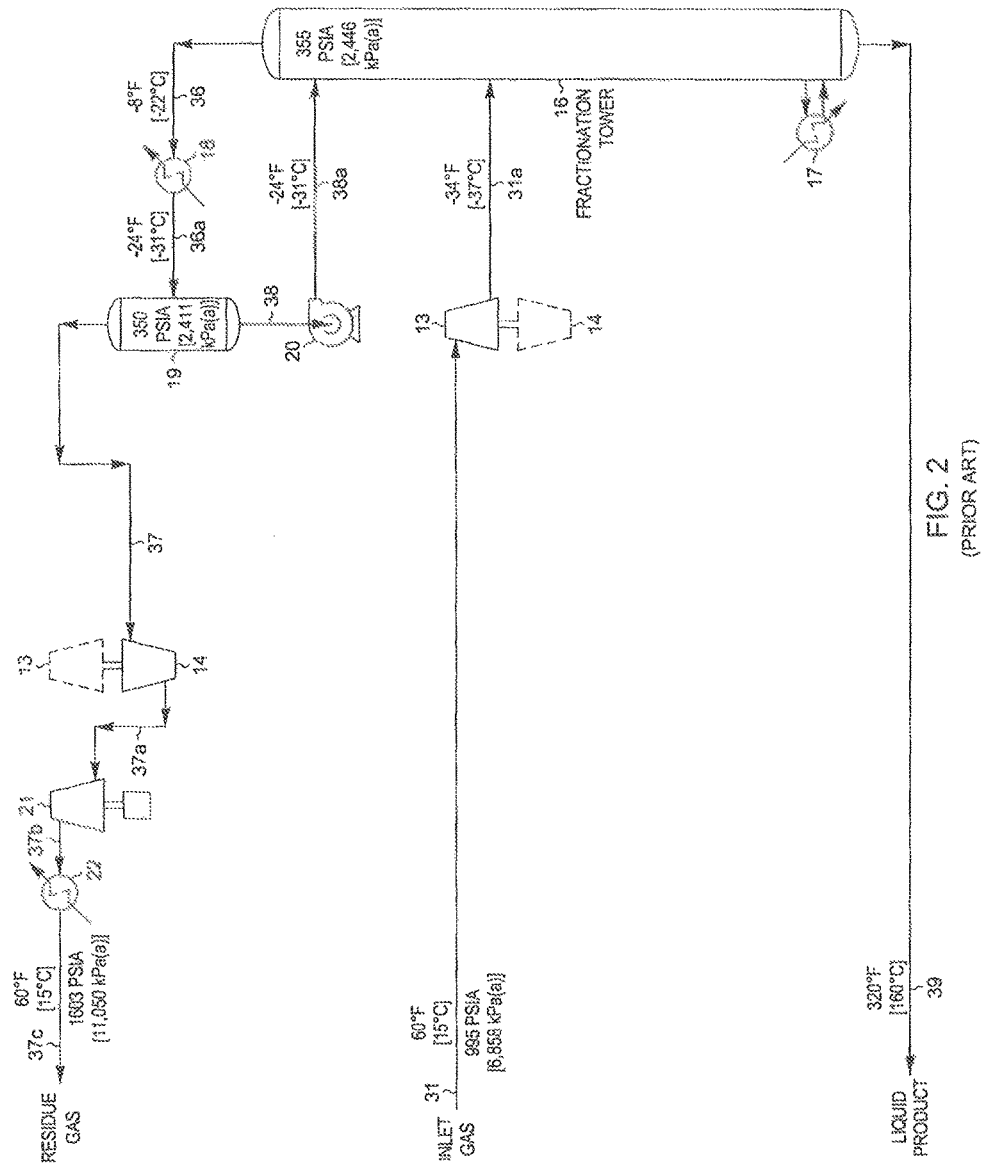

FIG. 2 is a process flow diagram showing the design of a processing plant to remove heavier hydrocarbon components from a natural gas stream using another prior art process. The process of FIG. 2 has been applied to the same feed gas composition and conditions as described previously for FIG. 1.

In this simulation of the process, inlet gas enters the plant at 60° F. [15° C.] and 995 psia [6,858 kPa(a)] as stream 31 and flows directly to work expansion machine 13 in which mechanical energy is extracted from the high pressure feed. The machine 13 expands the vapor substantially isentropically to the operating pressure (approximately 355 psia [2,446 kPa(a)]) of fractionation tower 16, with the work expansion cooling the expanded stream 31a to a temperature of approximately −34° F. [−37° C.] before it is supplied as feed to fractionation tower 16 at a mid-column feed point.

Liquid product stream 39 is stripped of the lighter hydrocarbon components and exits the bottom of tower 16 at 320° F. [160° C.]. The column overhead vapor (stream 36) is withdrawn from the top of tower 16 at −8° F. [−22° C.] and is cooled to −24° F. [−31° C.] and partially condensed (stream 36a) in heat exchanger 18 using a refrigerant, and the condensed liquid (stream 38) is separated from the uncondensed vapor (stream 37) in reflux separator 19. Liquid stream 38 is pumped by reflux pump 20 to a pressure slightly above the operating pressure of tower 16, and stream 38a is then supplied as cold top column feed (reflux) to tower 16. The residue gas (vapor stream 37) is re-compressed in two stages, compressor 14 driven by expansion machine 13 and compressor 21 driven by a supplemental power source. (In the FIG. 2 process, compressor 21 consists of two compression stages with intercooling between the stages.) After stream 37b is cooled in discharge cooler 22, the residue gas product (stream 37c) flows to the sales gas pipeline or to the liquefaction plant at 1603 psia [11,050 kPa(a)].

A summary of stream flow rates and energy consumption for the process illustrated in FIG. 2 is set forth in the following table:

TABLE II (FIG. 2)
Stream Flow Summary - Lb. Moles/Hr [kg moles/Hr]

| Stream | Methane | Ethane | Propane | Butanes | Pentanes+ | Total |
|---|---|---|---|---|---|---|
| 31 | 29,885 | 1,626 | 869 | 574 | 189 | 33,501 |
| 36 | 29,987 | 1,673 | 986 | 664 | 9 | 33,677 |
| 38 | 102 | 47 | 118 | 239 | 6 | 512 |
| 37 | 29,885 | 1,626 | 868 | 425 | 3 | 33,165 |
| 39 | 0 | 0 | 1 | 149 | 186 | 336 |

Recoveries*

| | |
|---|---|
| Butanes | 25.92% |
| Pentanes+ | 98.42% |

Power

| | | |
|---|---|---|
| Residue Gas Compression | 13,805 HP | [22,695 kW] |
| Refrigerant Compression | 1,261 HP | [2,073 kW] |
| Total Compression | 15,066 HP | [24,768 kW] |

*(Based on un-rounded flow rates)

DESCRIPTION OF THE INVENTION

Example 1

Figure 3:
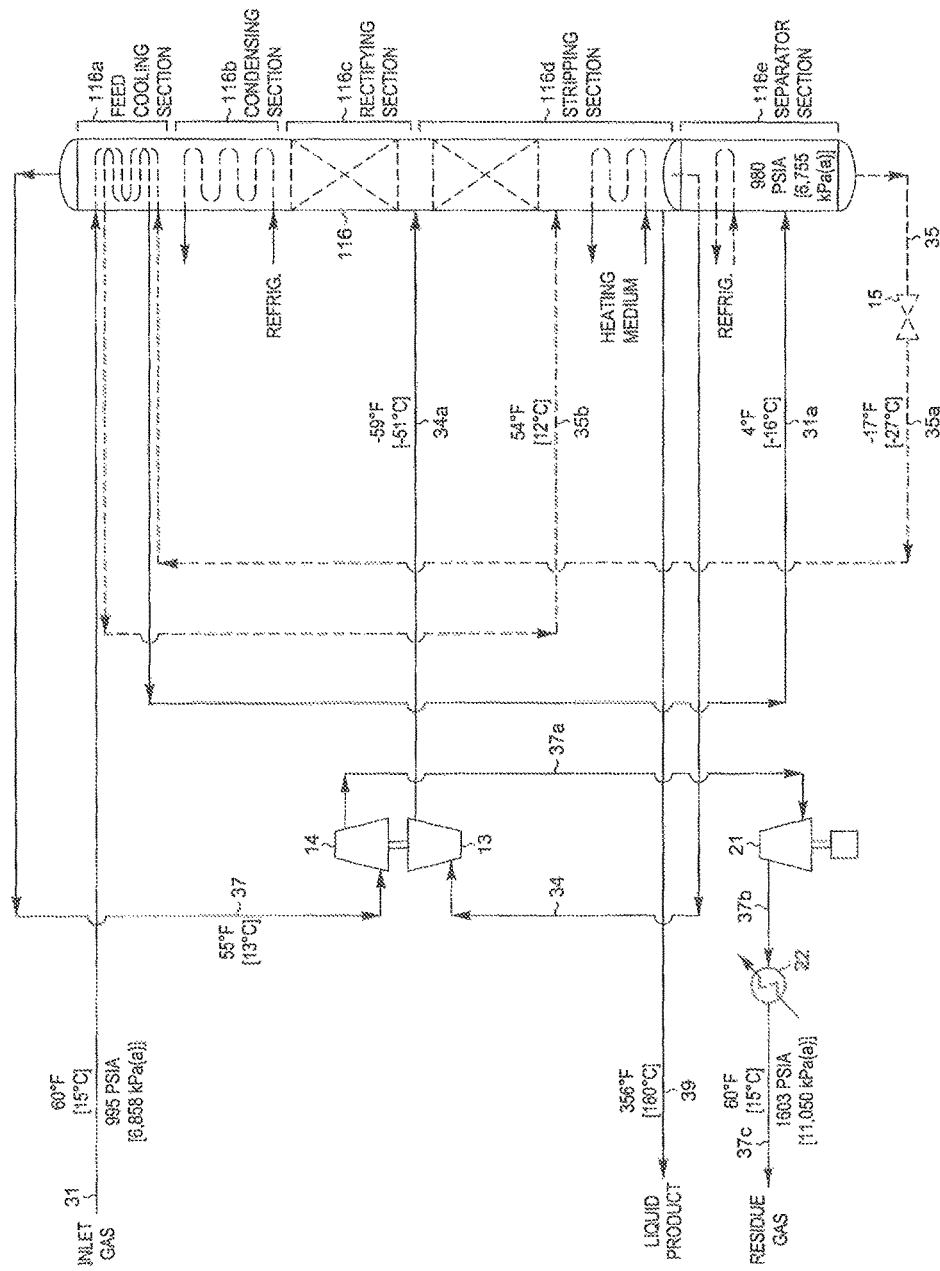
FIG. 3 is a flow diagram of a heavy ends removal plant for a natural gas liquefaction plant in accordance with the present invention.

FIG. 3 illustrates a flow diagram of a process in accordance with the present invention. The feed gas composition and conditions considered in the process presented in FIG. 3 are the same as those in FIG. 1. Accordingly, the FIG. 3 process can be compared with that of the FIG. 1 process to illustrate the advantages of the present invention.

In the process illustrated in FIG. 3, inlet gas enters the plant at 60° F. [15° C.] and 995 psia [6,858 kPa(a)] as stream 31 and is directed to a heat exchange means in feed cooling section 116a inside processing assembly 116. This heat exchange means may be comprised of a fin and tube type heat exchanger, a plate type heat exchanger, a brazed aluminum type heat exchanger, or other type of heat transfer device, including multi-pass and/or multi-service heat exchangers. The heat exchange means is configured to provide heat exchange between stream 31 flowing through one pass of the heat exchange means and flash expanded separator liquids (stream 35a) and a residue gas stream from condensing section 116b inside processing assembly 116. Stream 31 is cooled while heating the flash expanded separator liquids and the residue gas stream.

Separator section 116e has an internal head or other means to divide it from stripping section 116d, so that the two sections inside processing assembly 116 can operate at different pressures. The cooled stream 31a enters separator section 116e at 4° F. [−16° C.] and 980 psia [6,755 kPa(a)] where any condensed liquid (stream 35) is separated from the vapor (stream 34). Stream 35 exits separator section 116e and is expanded by expansion valve 15 to slightly above the operating pressure (470 psia [3,238 kPa(a)]) of stripping section 116d inside processing assembly 116, cooling stream 35a to −17° F. [−27° C.]. Stream 35a enters the heat exchange means in feed cooling section 116a to supply cooling to the feed gas as described previously, heating stream 35b to 54° F. [12° C.] before it enters below a mass transfer means inside stripping section 116d of processing assembly 116.

The vapor (stream 34) from separator section 116e enters a work expansion machine 13 in which mechanical energy is extracted from this portion of the high pressure feed. The machine 13 expands the vapor substantially isentropically to the operating pressure of rectifying section 116c inside processing assembly 116, with the work expansion cooling the expanded stream 34a to −59° F. [−51° C.]. The partially condensed expanded stream 34a is thereafter supplied as a feed between an absorbing means inside rectifying section 116c and the mass transfer means inside stripping section 116d of processing assembly 116.

A heat and mass transfer means is located below the mass transfer means inside stripping section 116d. The heat and mass transfer means may be comprised of a fin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a heating medium flowing through one pass of the heat and mass transfer means and a distillation liquid stream flowing downward from the lower region of the mass transfer means, so that the distillation liquid stream is heated. As the distillation liquid stream is heated, a portion of it is vaporized to form stripping vapors that rise upward to the mass transfer means as the remaining liquid continues flowing downward through the heat and mass transfer means. The heat and mass transfer means provides continuous contact between the stripping vapors and the distillation liquid stream so that it also functions to provide mass transfer between the vapor and liquid phases, stripping the liquid product stream 39 of lighter hydrocarbon components. The stripping vapors produced in the heat and mass transfer means continue upward to the mass transfer means in stripping section 116d to provide partial stripping of the lighter hydrocarbon components in the liquids flowing downward from the upper part of processing assembly 116.

Another heat and mass transfer means is located inside condensing section 116b, above the absorbing means inside rectifying section 116c of processing assembly 116. This heat and mass transfer means may also be comprised of a fin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a refrigerant stream flowing through one pass of the heat and mass transfer means and a distillation vapor stream arising from the upper region of the absorbing means flowing upward through the other pass, so that the distillation vapor stream is cooled by the refrigerant. As the distillation vapor stream is cooled, a portion of it is condensed and falls downward while the remaining distillation vapor stream continues flowing upward through the heat and mass transfer means. The heat and mass transfer means provides continuous contact between the condensed liquid and the distillation vapor stream so that it also functions to provide mass transfer between the vapor and liquid phases, thereby absorbing heavier hydrocarbon components from the distillation vapor stream to rectify it. The condensed liquid is collected from the bottom of the heat and mass transfer means and directed to the upper region of the absorbing means inside rectifying section 116c to provide partial rectification of the heavier hydrocarbon components in the vapors flowing upward from the lower part of processing assembly 116.

The absorbing means inside rectifying section 116c and the mass transfer means inside stripping section 116d each consist of a plurality of vertically spaced trays, one or more packed beds, or some combination of trays and packing. The trays and/or packing in rectifying section 116c and stripping section 116d provide the necessary contact between the vapors rising upward and liquid falling downward. The liquid portion of expanded stream 34a commingles with liquids falling downward from rectifying section 116c and the combined liquids continue downward into stripping section 116d, which vaporizes and strips the lighter hydrocarbon components from these liquids. The vapors arising from stripping section 116d combine with the vapor portion of expanded stream 34a and rise upward through rectifying section 116c, to be contacted with the cold liquid falling downward to condense and absorb the heavier hydrocarbon components from these vapors.

The distillation liquid flowing downward from the heat and mass transfer means in stripping section 116d inside processing assembly 116 has been stripped of the lighter hydrocarbon components so that it contains only the heavier hydrocarbon components that were in the natural gas feed stream (stream 31), whereupon it exits the lower region of stripping section 116d as stream 39 and leaves processing assembly 116 at 356° F. [180° C.]. The distillation vapor stream arising from condensing section 116b is heated in feed cooling section 116a as it provides cooling to stream 31 as described previously, whereupon residue gas stream 37 leaves processing assembly 116 at 55° F. [13° C.]. The residue gas stream is then re-compressed in two stages, compressor 14 driven by expansion machine 13 and compressor 21 driven by a supplemental power source. (In this example, compressor 21 consists of two compression stages with intercooling between the stages.) After cooling in discharge cooler 22, residue gas stream 37c flows to the sales gas pipeline or to the liquefaction plant at 1603 psia [11,050 kPa(a)].

A summary of stream flow rates and energy consumption for the process illustrated in FIG. 3 is set forth in the following table:

TABLE III (FIG. 3)
Stream Flow Summary - Lb. Moles/Hr [kg moles/Hr]

| Stream | Methane | Ethane | Propane | Butanes | Pentanes+ | Total |
|---|---|---|---|---|---|---|
| 31 | 29,885 | 1,626 | 869 | 574 | 189 | 33,501 |
| 34 | 29,571 | 1,555 | 769 | 428 | 77 | 32,758 |
| 35 | 314 | 71 | 100 | 146 | 112 | 743 |
| 37 | 29,885 | 1,626 | 868 | 423 | 3 | 33,164 |
| 39 | 0 | 0 | 1 | 151 | 186 | 337 |

Recoveries*

| Butanes | 26.26% |
|---|---|
| Pentanes+ | 98.42% |

Power

| Residue Gas Compression | 15,289 HP | [25,135 kW] |
|---|---|---|
| Refrigerant Compression | 846 HP | [1,391 kW] |
| Total Compression | 16,135 HP | [26,526 kW] |

*(Based on un-rounded flow rates)

A comparison of Tables I and III shows that, compared to the prior art, the compact processing assembly of the present invention maintains essentially the same butanes recovery and pentane+ recovery using slightly less power. However, the present invention offers at least two advantages over the prior art of FIG. 1. First, the compact arrangement of processing assembly 116 of the present invention replaces eight separate equipment items in the FIG. 1 prior art (heat exchangers 10 and 11, separator 12, fractionation tower 16, reboiler 17, reflux condenser 18, reflux separator 19, and reflux pump 20) with a single equipment item (processing assembly 116 in FIG. 3 of the present invention). This reduces the "footprint" of the processing plant and eliminates the interconnecting piping, reducing the capital cost of the processing plant itself and (more importantly) the capital cost of the platform or ship on which it is installed. Second, elimination of the interconnecting piping means that a processing plant using the present invention has far fewer flanged connections compared to the prior art, reducing the number of potential leak sources in the plant. Hydrocarbons are volatile organic compounds (VOCs), some of which are classified as greenhouse gases and some of which may be precursors to atmospheric ozone formation, which means the present invention reduces the potential for atmospheric releases that may damage the environment.

Example 2

Figure 4:
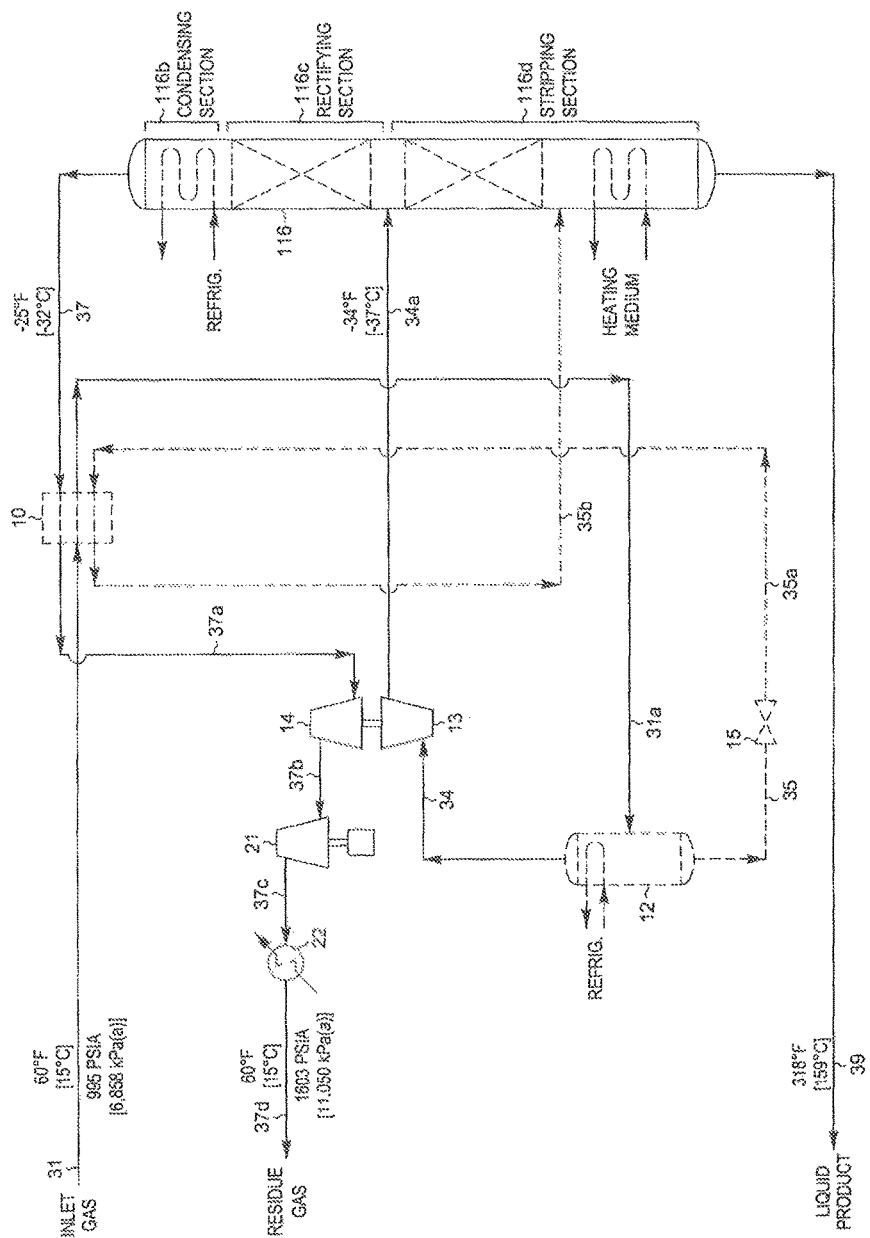
FIGS. 4 through 6 are flow diagrams illustrating alternative means of application of the present invention to heavy ends removal from a natural gas stream.

The present invention also offers advantages when circumstances favor expansion of the feed gas without cooling it first, as illustrated in FIG. 4. The feed gas composition and conditions considered in the process presented in FIG. 4 are the same as those in FIG. 2. Accordingly, the FIG. 4 process can be compared with that of the FIG. 2 process to further illustrate the advantages of the present invention.

In the process illustrated in FIG. 4, inlet gas enters the plant at 60° F. [15° C.] and 995 psia [6,858 kPa(a)] as stream 31 and is directed to work expansion machine 13 as stream 34. Mechanical energy is extracted from the high pressure feed as machine 13 expands the vapor substantially isentropically to the operating pressure (355 psia [2,446 kPa(a)]) of rectifying section 116c inside processing assembly 116, with the work expansion cooling the expanded stream 34a to −34° F. [−37° C.]. The partially condensed expanded stream 34a is thereafter supplied as feed between an absorbing means inside rectifying section 116c and a mass transfer means inside stripping section 116d of processing assembly 116.

A heat and mass transfer means is located below the mass transfer means inside stripping section 116d. The heat and mass transfer means is configured to provide heat exchange between a heating medium flowing through one pass of the heat and mass transfer means and a distillation liquid stream flowing downward from the lower region of the mass transfer means, so that the distillation liquid stream is heated. As the distillation liquid stream is heated, a portion of it is vaporized to form stripping vapors that rise upward to the mass transfer means as the remaining liquid continues flowing downward through the heat and mass transfer means. The heat and mass transfer means provides continuous contact between the stripping vapors and the distillation liquid stream so that it also functions to provide mass transfer between the vapor and liquid phases, stripping the liquid product stream 39 of lighter hydrocarbon components. The stripping vapors produced in the heat and mass transfer means continue upward to the mass transfer means in stripping section 116d to provide partial stripping of the lighter hydrocarbon components in the liquids flowing downward from the upper part of processing assembly 116.

Another heat and mass transfer means is located inside condensing section 116b, above the absorbing means inside rectifying section 116c of processing assembly 116. The heat and mass transfer means is configured to provide heat exchange between a refrigerant stream flowing through one pass of the heat and mass transfer means and a distillation vapor stream arising from the upper region of the absorbing means flowing upward through the other pass, so that the distillation vapor stream is cooled by the refrigerant. As the distillation vapor stream is cooled, a portion of it is condensed and falls downward while the remaining distillation vapor stream continues flowing upward through the heat and mass transfer means. The heat and mass transfer means provides continuous contact between the condensed liquid and the distillation vapor stream so that it also functions to provide mass transfer between the vapor and liquid phases, thereby absorbing heavier hydrocarbon components from the distillation vapor stream to rectify it. The condensed liquid is collected from the bottom of the heat and mass transfer means and directed to the upper region of the absorbing means inside rectifying section 116c to provide partial rectification of the heavier hydrocarbon components in the vapors flowing upward from the lower part of processing assembly 116.

The distillation liquid flowing downward from the heat and mass transfer means in stripping section 116d inside processing assembly 116 has been stripped of the lighter hydrocarbon components so that it contains only the heavier hydrocarbon components that were in the natural gas feed stream (stream 31), whereupon it exits the lower region of stripping section 116d as stream 39 and leaves processing assembly 116 at 318° F. [159° C.]. The distillation vapor stream arising from condensing section 116b is residue gas stream 37, which leaves processing assembly 116 at −25° F. [−32° C.]. The residue gas stream is re-compressed in two stages, compressor 14 driven by expansion machine 13 and compressor 21 driven by a supplemental power source. (In this example, compressor 21 consists of two compression stages with intercooling between the stages.) After cooling in discharge cooler 22, residue gas stream 37d flows to the sales gas pipeline or to the liquefaction plant at 1603 psia [11,050 kPa(a)].

A summary of stream flow rates and energy consumption for the process illustrated in FIG. 4 is set forth in the following table:

TABLE IV (FIG. 4)
Stream Flow Summary - Lb. Moles/Hr [kg moles/Hr]

| Stream | Methane | Ethane | Propane | Butanes | Pentanes+ | Total |
|---|---|---|---|---|---|---|
| 31/34 | 29,885 | 1,626 | 869 | 574 | 189 | 33,501 |
| 37 | 29,885 | 1,626 | 868 | 421 | 3 | 33,162 |
| 39 | 0 | 0 | 1 | 153 | 186 | 339 |

Recoveries*

| | |
|---|---|
| Butanes | 26.70% |
| Pentanes+ | 98.42% |

Power

| | | |
|---|---|---|
| Residue Gas Compression | 13,788 HP | [22,667 kW] |
| Refrigerant Compression | 1,269 HP | [2,086 kW] |
| Total Compression | 15,057 HP | [24,753 kW] |

*(Based on un-rounded flow rates)

A comparison of Tables II and IV shows that, compared to the prior art, the compact processing assembly of the present invention maintains essentially the same butanes recovery and pentane+ recovery using slightly less power. However, the present invention offers at least two advantages over the prior art of FIG. 2. First, the compact arrangement of processing assembly 116 of the present invention replaces five separate equipment items in the FIG.

2 prior art (fractionation tower 16, reboiler 17, reflux condenser 18, reflux separator 19, and reflux pump 20) with a single equipment item (processing assembly 116 in FIG. 4 of the present invention). This reduces the "footprint" of the processing plant and eliminates the interconnecting piping, reducing the capital cost of the processing plant itself and (more importantly) the capital cost of the platform or ship on which it is installed. Second, elimination of the interconnecting piping means that a processing plant using the present invention has far fewer flanged connections compared to the prior art, reducing the number of potential leak sources in the plant. Hydrocarbons are volatile organic compounds (VOCs), some of which are classified as greenhouse gases and some of which may be precursors to atmospheric ozone formation, which means the present invention reduces the potential for atmospheric releases that may damage the environment.

Other Embodiments

Figure 6:
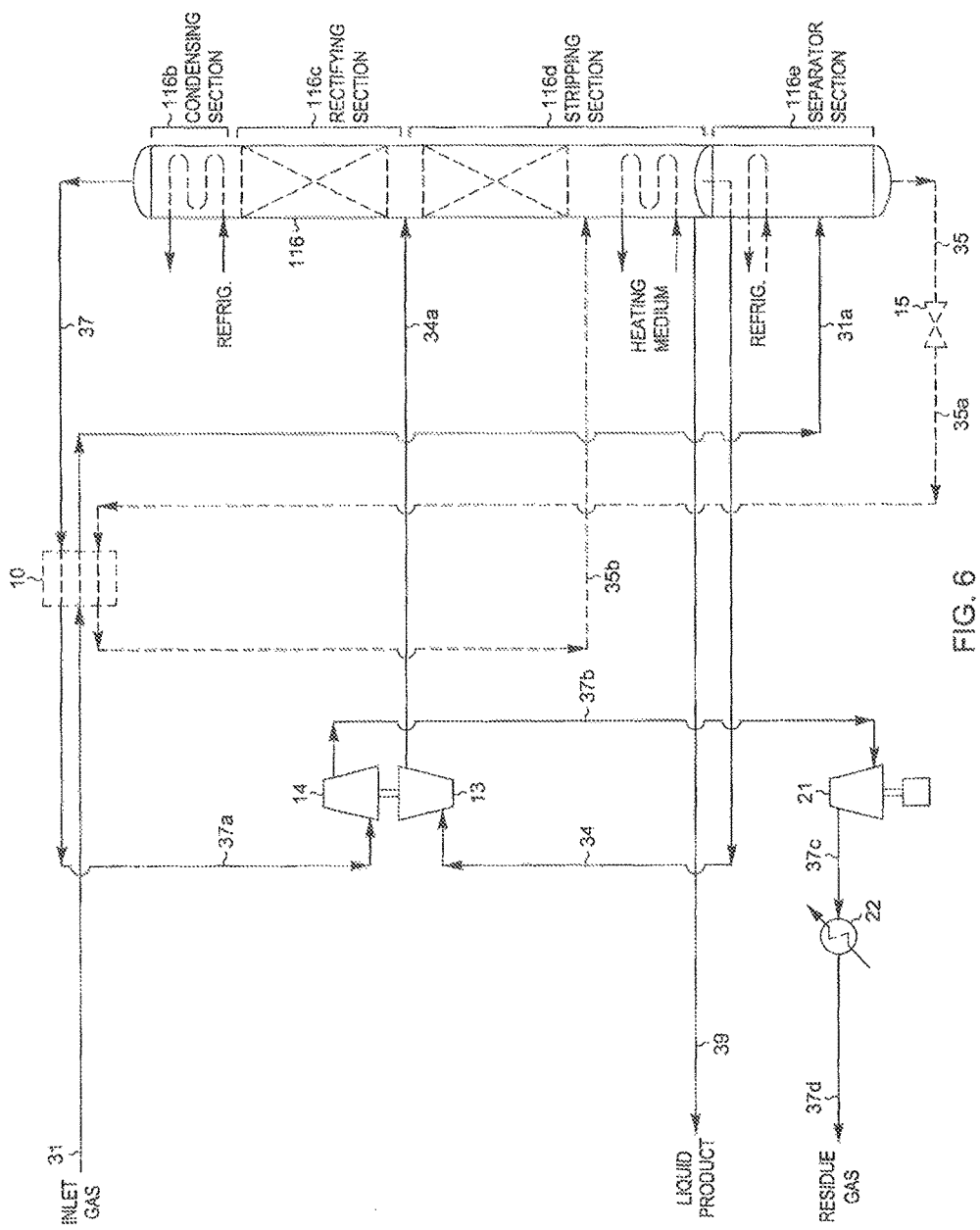

Some circumstances may favor eliminating feed cooling section 116a from processing assembly 116 in order to reduce the height of processing assembly 116. As shown in FIGS. 4 and 6, in such cases heat exchanger 10 can be used to provide the cooling of the feed gas (stream 31). In other circumstances, it may be advantageous not to cool the feed gas at all, so that stream 34 is warmer and its work expansion in expansion machine 13 generates more power for compressor 14. In such circumstances, heat exchanger 10 in FIGS. 4 and 6 may not be required.

Figure 5:
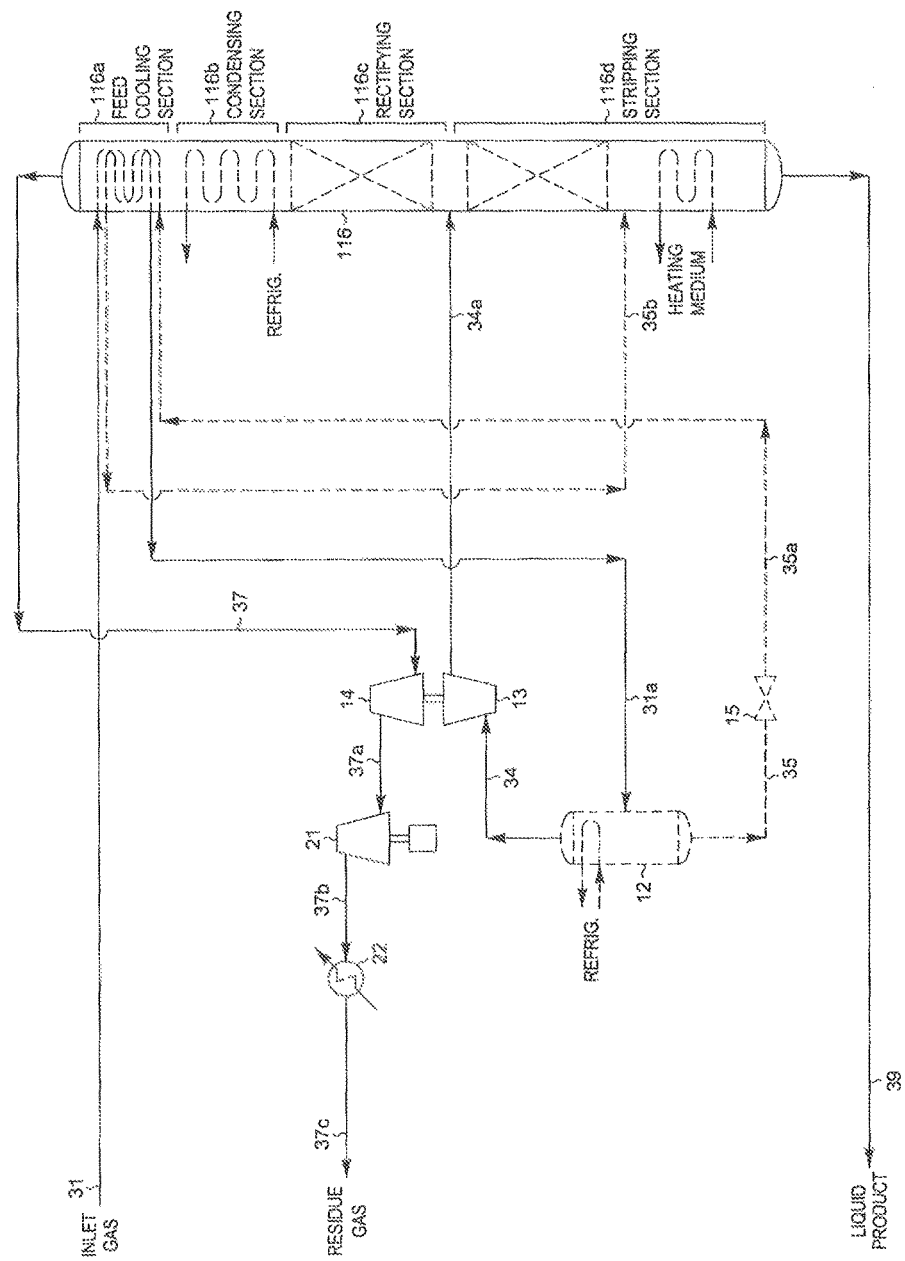

In some circumstances, it may be advantageous to use an external separator vessel to separate cooled feed stream 31a, rather than including separator section 116e in processing assembly 116. As shown in FIGS. 4 and 5, separator 12 can be used to separate cooled feed stream 31a into vapor stream 34 and liquid stream 35.

Depending on the quantity of heavier hydrocarbons in the feed gas and the feed gas pressure, the cooled feed stream 31a entering separator section 116e in FIGS. 3 and 6 or separator 12 in FIGS. 4 and 5 may not contain any liquid (because it is above its dewpoint, or because it is above its cricondenbar). In such cases, there is no liquid in stream 35 (as shown by the dashed lines). In such circumstances, separator section 116e in processing assembly 116 (FIGS. 3 and 6) or separator 12 (FIGS. 4 and 5) may not be required.

Feed gas conditions, plant size, available equipment, or other factors may indicate that elimination of work expansion machine 13, or replacement with an alternate expansion device (such as an expansion valve), is feasible. Although individual stream expansion is depicted in particular expansion devices, alternative expansion means may be employed where appropriate. For example, conditions may warrant work expansion of the separator liquid (stream 35).

In accordance with the present invention, the use of external refrigeration to supplement the cooling available to the inlet gas from the distillation vapor and separator liquid streams may be employed, particularly in the case of a rich inlet gas. In such cases, a heat and mass transfer means may be included in separator section 116e (or a collecting means in such cases when the cooled feed stream 31a contains no liquid) as shown by the dashed lines in FIGS. 3 and 6, or a heat and mass transfer means may be included in separator 12 as shown by the dashed lines in FIGS. 4 and 5. This heat and mass transfer means may be comprised of a fin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a refrigerant stream (e.g., propane) flowing through one pass of the heat and mass transfer means and the vapor portion of stream 31a flowing upward, so that the refrigerant further cools the vapor and condenses additional liquid, which falls downward to become part of the liquid removed in stream 35. Alternatively, conventional gas chiller(s) could be used to cool stream 31a with refrigerant before stream 31a enters separator section 116e (FIGS. 3 and 6) or separator 12 (FIGS. 4 and 5).

Depending on the type of heat transfer device selected for the heat exchange means in feed cooling section 116a and the type of heat and mass transfer device selected for the heat and mass transfer means in condensing section 116b, it may be possible to combine these in a single multi-pass and/or multi-service heat and mass transfer device. In such cases, the multi-pass and/or multi-service heat and mass transfer device will include appropriate means for distributing, segregating, and collecting streams 31/31a, streams 35a/35b, and the distillation vapor stream in order to accomplish the desired cooling and heating.

While there have been described what are believed to be preferred embodiments of the invention, those skilled in the art will recognize that other and further modifications may be made thereto, e.g. to adapt the invention to various conditions, types of feed, or other requirements without departing from the spirit of the present invention as defined by the following claims.

We claim:

1. An apparatus for the separation of a gas stream containing methane, $C_2$ components, $C_3$ components, $C_4$ components, $C_5$ components, and heavier hydrocarbon components into a volatile residue gas fraction and a relatively less volatile fraction containing a major portion of said $C_5$ components and heavier hydrocarbon components comprising (1) expansion means connected to receive said gas stream under pressure and expand it to a lower pressure;

(2) a processing assembly connected to said expansion means to receive said expanded gas stream as a feed between an absorbing means and a mass transfer means housed in said processing assembly, said absorbing means being located above said mass transfer means;

(3) vapor collecting means housed in said processing assembly and connected to said absorbing means to receive a first distillation vapor stream from an upper region of said absorbing means;

(4) first heat and mass transfer means housed in said processing assembly and connected to said vapor collecting means to receive said first distillation vapor stream and cool it while simultaneously condensing the less volatile components from said first distillation vapor stream, thereby forming a condensed stream and a second distillation vapor stream, whereupon said second distillation vapor stream is discharged from said processing assembly as said volatile residue gas fraction;

(5) said absorbing means being further connected to said first heat and mass transfer means to receive said condensed stream as a top feed thereto;

(6) liquid collecting means housed in said processing assembly and connected to said mass transfer means to receive a distillation liquid stream from a lower region of said mass transfer means;

(7) second heat and mass transfer means housed in said processing assembly and connected to said liquid collecting means to receive said distillation liquid stream and heat it, thereby simultaneously stripping the more volatile components from said distillation liquid stream, whereupon said heated and stripped distillation liquid stream is discharged from said processing assembly as said relatively less volatile fraction; and (8) control means adapted to maintain the temperature of said second distillation vapor stream at a temperature whereby the major portion of said $C_5$ components and heavier hydrocarbon components are recovered in said relatively less volatile fraction.

2. The apparatus according to claim 1 wherein
(a) one or more heat exchange means is connected to receive said gas stream under pressure and cool it; and
(b) said expansion means is adapted to be connected to said one or more heat exchange means to receive said cooled gas stream and expand it to said lower pressure, whereupon said expanded cooled gas stream is supplied to said processing assembly as said feed between said absorbing means and said mass transfer means.

3. The apparatus according to claim 1 wherein
(a) one or more heat exchange means is connected to receive said gas stream under pressure and cool it sufficiently to partially condense it;
(b) a separating means is connected to said one or more heat exchange means to receive said partially condensed gas stream and separate it into a vapor stream and at least one liquid stream;
(c) said expansion means is adapted to be connected to said separating means to receive said vapor stream and expand it to said lower pressure, whereupon said expanded vapor stream is supplied to said processing assembly as said feed between said absorbing means and said mass transfer means;
(d) an additional expansion means is connected to said separating means to receive at least a portion of said at least one liquid stream and expand it to said lower pressure, thereby forming an expanded liquid stream; and
(e) a heating means is connected to said additional expansion means to receive said expanded liquid stream and heat it, said heating means being further connected to said processing assembly to supply said heated expanded liquid stream as an additional feed to said processing assembly below said mass transfer means.

4. The apparatus according to claim 2 wherein
(i) said one or more heat exchange means is housed in said processing assembly; and
(ii) said one or more heat exchange means is further connected to said first heat and mass transfer means to receive said second distillation vapor stream and heat it, thereby to supply at least a portion of the cooling of element (a), and thereafter discharging said heated second distillation vapor stream from said processing assembly as said volatile residue gas fraction.

5. The apparatus according to claim 3 wherein
(i) said one or more heat exchange means is housed in said processing assembly; and
(ii) said one or more heat exchange means is further connected to said first heat and mass transfer means to receive said second distillation vapor stream and heat it, thereby to supply at least a portion of the cooling of element (a), and thereafter discharging said heated second distillation vapor stream from said processing assembly as said volatile residue gas fraction.

6. The apparatus according to claim 3 or 5 wherein said separating means is housed in said processing assembly.

7. The apparatus according to claim 2 or 4 wherein
(a) a collecting means is housed in said processing assembly;
(b) an additional heat and mass transfer means is included inside said collecting means, said additional heat and mass transfer means including one or more passes for an external refrigeration medium;
(c) said collecting means is connected to said one or more heat exchange means to receive said cooled gas stream and direct it to said additional heat and mass transfer means to be further cooled by said external refrigeration medium; and
(d) said expansion means is adapted to be connected to said collecting means to receive said further cooled gas stream and expand it to said lower pressure, whereupon said expanded further cooled gas stream is supplied to said processing assembly as said feed between said absorbing means and said mass transfer means.

8. The apparatus according to claim 3 or 5 wherein
(a) an additional heat and mass transfer means is included inside said separating means, said additional heat and mass transfer means including one or more passes for an external refrigeration medium;
(b) said vapor stream is directed to said additional heat and mass transfer means to be cooled by said external refrigeration medium to form additional condensate; and
(c) said additional condensate becomes a part of said at least one liquid stream separated therein.

9. The apparatus according to claim 6 wherein
(a) an additional heat and mass transfer means is included inside said separating means, said additional heat and mass transfer means including one or more passes for an external refrigeration medium;
(b) said vapor stream is directed to said additional heat and mass transfer means to be cooled by said external refrigeration medium to form additional condensate; and
(c) said additional condensate becomes a part of said at least one liquid stream separated therein.

* * * * *